United States Patent [19]

Finkelman et al.

[11] Patent Number: 4,584,273

[45] Date of Patent: Apr. 22, 1986

[54] METHOD FOR THE PRODUCTION OF PHENYLALANINE AMMONIA-LYASE BY FERMENTATION

[75] Inventors: Malcolm A. J. Finkelman, Gaithersburg; Huei-Hsuing Yang, Rockville, both of Md.

[73] Assignee: Genex Corporation, Rockville, Md.

[21] Appl. No.: 547,139

[22] Filed: Oct. 31, 1983

[51] Int. Cl.[4] .......................... C12N 9/88; C12P 13/22
[52] U.S. Cl. .................................... 435/232; 435/108; 435/801
[58] Field of Search .......................... 435/232, 108, 801

[56] References Cited

U.S. PATENT DOCUMENTS

| | | | |
|---|---|---|---|
| 3,791,924 | 2/1974 | Ogata et al. | 195/29 |
| 3,917,511 | 11/1975 | Nakayama et al. | 195/29 |
| 3,957,580 | 5/1976 | Nelson | 195/59 |
| 4,375,515 | 3/1983 | Patel et al. | 435/189 |

FOREIGN PATENT DOCUMENTS

| | | | |
|---|---|---|---|
| 53-96388 | 8/1978 | Japan . | |
| 1489468 | 10/1977 | United Kingdom | 101/8 |

OTHER PUBLICATIONS

"L-Phenylalanine Ammonia-Lyase, II, Mechanism and Kinetic Properties of the Enzyme from Potato Tubers," by Havir and Hanson, *Biochemistry* vol. 7, No. 5, May 1968.

*Primary Examiner*—Lionel M. Shapiro
*Attorney, Agent, or Firm*—Bernard, Rothwell & Brown

[57] ABSTRACT

A method for the production of the enzyme, phenylalanine ammonia-lyase (PAL), by fermentation, wherein the stability and useful life of the enzyme are improved by maintaining PAL-containing media in substantially anaerobic, static conditions. PAL is useful for catalyzing the conversion of t-cinnamic acid and ammonia to L-phenylalanine.

14 Claims, No Drawings

METHOD FOR THE PRODUCTION OF PHENYLALANINE AMMONIA-LYASE BY FERMENTATION

BACKGROUND OF THE INVENTION

Enzymatic methods using L-phenylalanine ammonia-lyase for the conversion of trans-cinnamic acid to L-phenylalanine generally comprise the steps of (a) aerobically propagating a phenylalanine ammonia-lyase (hereinafter PAL)-producing microorganism in an aqueous nutrient medium until substantial amounts of PAL are produced, (b) contacting the cells of the PAL-producing microorganism from step (a), either as the whole culture broth or separated cells therefrom, or the isolated enzyme, with ammonium ions and trans-cinnamate ions and allowing the reaction to proceed under controlled temperature and pH conditions until the conversion to L-phenylalanine is substantially complete and (c) separating and recovering the L-phenylalanine from the reaction mixture.

The foregoing method is described, for example, in British Pat. No. 1,489,468 (Oct. 19, 1977). A drawback to the use of this process for commercial production has been the relative instability of PAL, and its inhibition by the substrate, t-cinnamic acid. To drive the reaction toward the production of L-phenylalanine and to counteract the effects of substrate inhibition, the above-mentioned British patent describes a process which employs large masses of PAL-containing cells and excess concentrations of ammonium ions.

Yamada, S. et al. (*Appl. and Environ. Microbiol.*, 42, 773–778 (1981)) have described the production of L-phenylalanine from t-cinnamic acid using PAL-containing *Rhodotorula glutinis* cells. They speculated that the lack of previous practical application of this process was attributable to the low activity and instability of microbial PAL. Yamada, et al. found that L-isoleucine had a stabilizing effect on PAL, and extended the useful period of activity of the enzyme. These authors further observed the inhibitive effect of the substrate, noting that at practical concentrations of t-cinnamic acid (150 mM), the rate of conversion of L-phenylalanine was reduced to one-half the maximum rate.

Despite the improvements described above, as far as is known, the PAL process has not been used for the commercial production of L-phenylalanine. The instability and low activity of the enzyme has continued to be a disadvantage of this process.

SUMMARY OF THE INVENTION

In accordance with the present invention, an improved process for producing the enzyme, phenylalanine ammonialyase, involves cultivating a PAL-producing microorganism under aerobic, growth promoting conditions; inducing said microorganism to make PAL under PAL-producing conditions; and subjecting the PAL-containing medium to substantially anaerobic, static conditions.

It has been found that reducing aeration and agitation of the fermentation medium following PAL induction improves the stability and prolongs the activity of the enzyme.

DESCRIPTION OF THE INVENTION

In copending U.S. patent application Ser. No. 547,258, filed Oct. 31, 1983, it is disclosed that phenylalanine ammonialyase is sensitive to degradation in the presence of oxygen and under the influence of mechanical agitation. Accordingly, that patent application teaches that the stability and useful life of the enzyme can be improved if the bioconversion reaction is conducted under substantially anaerobic, static conditions.

In accordance with the present invention, the fermentative process for producing PAL has been improved by maintaining the fermentation medium under substantially anaerobic, static conditions following PAL induction. The exact mechanisms by which these conditions improve the stability of the enzyme are not well understood, but in addition to reducing the chemical and mechanical effects of oxygen and agitation, it is believed that these conditions also reduce the metabolic activities of the cells, with a concomitant decrease in the proteolytic breakdown of the enzyme.

Introducing substantially anaerobic, static conditions in the fermentation medium following PAL induction can significantly improve the overall efficiency and yields of a process for producing L-phenylalanine using this enzyme. There is usually a delay between the production of PAL and the use of the enzyme for the production of L-phenylalanine. This delay can result from cell harvesting or storage procedures. Substantial enzyme losses can occur during the period of delay.

Anaerobic conditions may be achieved by various means, such as sparging with an inert gas (e.g., nitrogen), reducing or eliminating agitation, and limiting any air head-space over the surface of the cell-containing medium. Two or more of these techniques may advantageously be combined.

Static conditions are achieved by reducing agitation to a minimal level sufficient to maintain substantial homogeneity. Some agitation is generally desired to prevent settling of solids or solid-bound reaction components.

Any PAL-producing microorganism can be used in the process of this invention. Preferred microorganisms include PAL-producing strains of bacteria of the genus Streptomyces and yeasts of the genera, Rhodotorula, Rhodosporidium and Sporobolomyces. Such microorganisms are described, for example, in U.S. patent application Ser. No. 547,129, filed Oct. 31, 1983, incorporated herein by reference. Most preferred microorganisms are strains of *Rhodotorula rubra* and *Rhodosporidium toruloides* described in Example I of that application.

The PAL-producing microorganisms employed in the method of this invention require oxygen for growth; therefore, the cells are initially cultivated under aerobic, growth-promoting conditions. Generally, conventional procedures are employed for growing the cells. Cells are inoculated into a nutritional medium containing assimilable sources of carbon and nitrogen and essential vitamins, minerals and other growth factors. Suitable carbon sources can include various refined or crude carbohydrates such as glucose, sucrose, molasses, starches, grains and the like. A preferred carbon source is glucose. Nitrogen sources include inorganic ammonium salts, such as ammonium phosphate, ammonium sulfate, ammonium acetate, ammonium citrate, ammonium nitrate and the like and organic nitrogeneous substances such as soybean meal, meat infusions, amino acids, corn steep liquor, protein hydrolyzates, peptone, yeast extracts, and the like. A preferred nitrogen source for the process of this invention is yeast extract, and this nutrient may advantageously be combined with diammonium phosphate which supplies both nitrogen and phosphorous.

Vitamins, minerals and other growth factors may be supplied by the carbon and nitrogen sources (e.g., via the yeast extract) or may be supplied separately. These components can vary with the particular microorganism employed. Typically, trace minerals such as zinc, manganese, iron, cobalt, and calcium can be supplied in growth-promoting amounts as inorganic salts. These minerals may, for example, be supplied with process water, e.g., tap water, sea water, etc. Nutrient media of the type described are well known, and can vary in composition widely.

After growing the cells to the desired cell density under aerobic conditions, they are induced to make PAL under aerobic, PAL-producing conditions. PAL induction is generally achieved by adding small amounts of a compound that acts as a substrate for the PAL. L-Phenylalanine is a good PAL inducer, and a number of analogs of L-phenylalanine also induce the synthesis of this enzyme. For example, D,L-phenylalanine, L-tyrosine, and D,L-tyrosine can be employed for this purpose. In addition, it has been discovered that various crude nitrogen sources can be used for PAL induction. Such crude nitrogen sources include hydrolyzed proteins which contain substantial amounts of L-phenylalanine or L-tyrosine. Casein and blood hydrolyzates can advantageously be used as crude nitrogen sources for the induction of PAL synthesis.

The PAL inducer is added to the cells in a PAL-inducing amount, which generally ranges from about 0.1 to 10 g/l of the fermentation medium. Preferably, the PAL inducer is employed at a concentration from about 4 to about 8 g/l of the fermentation medium. During this step, PAL-inducing conditions of temperature and pH, aeration and agitation are maintained. The temperature and pH are generally maintained within physiologically compatible limits during PAL induction. Somewhat reduced temperatures, e.g. from about 15° C. to about 25° C. are preferred, because at these lower temperatures, enzyme stability is improved and the rate of consumption of the PAL inducer is decreased. A preferred pH for the PAL induction ranges from about 5.5 to about 7.5, where relatively higher PAL levels are achieved.

If the cells employed are sensitive to catabolic repression of PAL synthesis, then, prior to induction, means should be employed to reduce or eliminate catabolites and their precursors from the medium. This may be accomplished by separating cells from the medium, washing them and suspending them in a catabolite-free medium. Alternatively, the cells can be allowed to grow until the nutrients are substantially exhausted before the PAL induction procedure is initiated.

The cells are advantageously cultivated under PAL-inducing conditions until the PAL activity reaches at least about 0.5 units per ml, preferably at least about 2.0 units per ml. It has been observed that under these conditions, the PAL activity increases to a certain point and then begins to diminish. PAL produced by these procedures may be employed to produce L-phenylalanine from t-cinnamic acid and ammonia.

Following PAL induction and accumulation of the desired level of PAL activity, the substantially anaerobic, static conditions are introduced in the fermentation medium. Generally these conditions are achieved by stopping aeration and agitation and sparging the medium with an inert gas, such as nitrogen. Typically, in a batch reaction system, the cells will be harvested by centrifugation and transferred to a bioreaction vessel. In such case, the substantially anaerobic, static conditions are also maintained following harvesting.

As indicated above, phenylalanine ammonia-lyase has been found to be quite sensitive to degradation in the presence of oxygen and under the influence of agitation. Whereas agitation in conventional reaction vessels (e.g. deep tank fermentors) is conducted at a power level of from about 0.5 to 1 watt per liter, agitation power input for the fermentation mixtures of the present invention advantageously averages below about 400 milliwatts per liter, preferably below about 100 milliwatts per liter. Higher levels of power input, for example, up to about 5 watts per liter, can be used, but in such cases, the agitation is applied intermittently, e.g., 30 seconds of mixing at intervals of 2 hours.

The nature of the agitation can also affect enzyme stability. A low shear mixing is preferred. This type of agitation can be conveniently provided by periodically sparging the reaction mixture with an inert gas, such as nitrogen. In addition, mechanical agitators designed for low shear mixing can be employed. Generally, only enough agitation is employed to maintain a substantially homogeneous mixture.

Phenylalanine ammonia-lyase produced by the process of this invention is used to catalyze the conversion of t-cinnamic acid and ammonia to L-phenylalanine. This conversion is accomplished by contacting the enzyme, in whole cells, as the isolated enzyme or in immobilized form, with a substrate solution under PAL-producing conditions. A particularly preferred procedure for conducting the conversion reaction is described in the aforementioned U.S. patent application Ser. No. 547,258, filed Oct. 31, 1983, incorporated herein by reference.

The bioreaction is continued until substantial amounts of L-phenylalanine have accumulated in the reaction mixture. Generally recovery procedures are initiated when the L-phenylalanine concentrations reach about 30 g/l, preferably about 45–50 g/l. L-Phenylalanine can be recovered from the reaction mixture by any suitable means. For example, solids can be removed by filtration or centrifugation to produce a clarified solution, and L-phenylalanine can be precipitated from that solution by adjusting the pH to the isoelectric point of L-phenylalanine, i.e., about 5.5.

The following examples further illustrate the present invention. These examples are not to be construed as limiting the present invention.

EXAMPLE I

This example describes a fermentative procedure for producing phenylalanine ammonia-lyase in accordance with the present invention. *Rhodotorula rubra,* strain (NRRL Y-15597) was grown on a malt agar slant at 30° C. The agar slant medium contained 1% malt extract (Difco), 1.5% agar (Difco), and had a pH of 6.0.

25 ml of a seed medium containing 1% w/v yeast extract, 7% v/v high fructose corn syrup, (sterilized separately), pH 6.0, were added to a 250 ml shake flask. This medium was inoculated with a loop from the slant culture, and incubated for 24 hours at 30° C. on a gyrotory shaker.

To a 4 liter baffled shake flask, 550 ml of the above-described seed medium was added. This medium was inoculated by transferring the entire 25 ml from the first shake flask. The 4 liter shake flask was incubated for 24 hours at 30° C. on a gyratory shaker, until the optical density at 560 nm was at least 40.

The entire contents of the 4 liter shake flask was added to a 14 liter jar fermentor containing 9.5 liters of the above-described seed medium. After 14 hours of incubation with aeration and agitation at 30° C., the optical density at 560 nm of the jar fermentor was at least 40.

The entire contents of the jar fermentor were then used to innoculate a 250 liter fermentor containing 136 liters of a production medium. The production medium had the following composition:

| High Fructose Corn Syrup | 15 grams/liter |
|---|---|
| Yeast Extract | 4.5 grams/liter |
| Diammonium Phosphate | 1.8 grams/liter |
| L-phenylalanine | 8.5 grams/liter |
| Silicone Antifoam | 100 ppm |

The volume after innoculation was about 150 liters. The pH of the fermentor was controlled at 6.0 by additions of 29% aqueous ammonia or 10% sulfuric acid. This medium was agitated, and was aerated at a rate of 1 vvm. The temperature was maintained at 30° C.

After the optical density at 560 nm of the fermentor contents reached 20, high fructose corn syrup was added in an amount that resulted in a concentration of 15 grams per liter. At an optical density of 560 nm of 30, yeast extract was added in an amount that resulted in a concentration of 9 grams/liter. The final volume after all additions was about 165 liters.

After about 20 hours, the PAL activity of the fermentation medium reached a peak of 2140 units/liter. At this point, the air supply was turned off, the agitator was stopped, and the culture was de-aerated with nitrogen gas. The fermentation medium was maintained under these conditions until the cells were harvested by passing the culture through a disk-bowl centrifuge.

EXAMPLE II

This example describes an experiment demonstrating the induction of PAL production using a crude nitrogen source. The nitrogen source employed in this experiment was a hydrolyzed casein sold by Sheffield Chemical, Memphis, Tenn., U.S.A., under the name N-Z Amine. The efficiency of this crude nitrogen in inducing PAL production was compared to that of L-phenylalanine.

The *Rhodotorula rubra* strain described in Example I was grown in 10 liters of fermentation media which contained soy peptone (30 g/l) and various amounts of corn steep liquor with either hydrolyzed casein or L-phenylalanine. The fermentation was conducted at 30° C. The pH of the medium was maintained at 6.0 by additions of either 29% aqueous ammonia or 10% sulfuric acid. The mixture was aerated at 0.8 fermentor volumes of air per minute and was agitated by means of a mechanical agitator. The results of this experiment are shown in Table I below. These results demonstrate that a crude nitrogen source can be substituted for L-phenylalanine as a PAL-inducer.

TABLE I

| Fermentation Medium | | At Peak PAL Activity | | Final Cell Concentration DCW |
|---|---|---|---|---|
| | | Cell Concentration Dry Cell Wt. (DCW) | PAL Activity units/g DCW | |
| Corn Steep Liquor | Hydrolyzed Casein | | | |
| 0 g/l | 15 g/l | 8.8 g/l | 49.0 | 9.6 g/l |
| 2 | 15 | 8.8 | 56 | 10.0 |
| 4 | 15 | 9.5 | 52 | 10.2 |
| 10 | 15 | 9.2 | 57 | 10.6 |
| | L-Phenyl-alanine | | | |
| 0 g/l | 1.5 g/l | 7.0 g/l | 49 | 7.7 g/l |
| 2 | 1.5 | 7.2 | 65 | 7.6 |
| 4 | 1.5 | 7.0 | 46 | 7.4 |
| 10 | 1.5 | 7.9 | 53 | 8.6 |

We claim:

1. A process for producing phenylalanine ammonia-lyase, which comprises cultivating a phenylalanine ammonia-lyase-producing microorganism of the genus Rhodotorula or Rhodosporidium under aerobic growth-promoting conditions; inducing said microorganism to make phenylalanine ammonia-lyase under phenylalanine ammonia-lyase-producing conditions; and, following induction of phenylalanine ammonia-lyase production, subjecting the resulting fermentation medium to substantially anaerobic-static conditions.

2. The method of claim 1, wherein said phenylalanine ammonia-lyase-producing microorganism is a bacterium of the genus Streptomyces or a yeast of the genus Rhodotorula, Rhodosporidium or Sporobolomyces.

3. The process of claim 2, wherein said microorganism is a phenylalanine ammonia-lyase-producing strain of *Rhodotorula rubra* or *Rhodosporidium toruloides*.

4. The process of claim 1, 2 or 3 wherein the anaerobic conditions are at least partially achieved by sparging the fermentation medium with an inert gas.

5. The process of claim 1, 2 or 3 wherein the substantially static conditions are achieved by periodically sparging the fermentation medium with an inert gas.

6. The process of claim 1, 2 or 3, wherein the substantially static conditions are achieved by a low level of mechanical agitation using a low shear agitator.

7. The process of claim 6, wherein the agitation power input averages less than about 400 milliwatts per liter of fermentation medium.

8. The process of claim 6, wherein the agitation power input averages less than about 100 milliwatts per liter of fermentation medium.

9. The process of claim 4, wherein said microorganism is cultivated in a nutritional medium containing assimilable sources of carbon and nitrogen and essential vitamins, minerals and growth factors.

10. The process of claim 9, wherein said carbon source is glucose.

11. The process of claim 9, wherein said nitrogen source includes a yeast extract and an inorganic ammonium salt.

12. The process of claim 4, wherein the microorganism is induced to make phenylalanine ammonia-lyase by adding a phenylalanine ammonia-lyase inducing amount of L-phenylalanine, D,L-phenylalanine, D-tyrosine or a hydrolyzed protein which contains substantial amounts of L-phenylalanine or L-tyrosine.

13. The process of claim 12, wherein the phenylalanine ammonia-lyase inducer is L-phenylalanine.

14. The process of claim 12, wherein the phenylalanine ammonia-lyase inducer is hydrolyzed casein.

* * * * *